United States Patent
Ito et al.

(10) Patent No.: US 6,951,750 B2
(45) Date of Patent: Oct. 4, 2005

(54) PROLIDASE AND ITS GENE AND METHOD FOR PRODUCING PROLIDASE

(75) Inventors: Kotaro Ito, Chiba (JP); Takeharu Nakahara, Chiba (JP); Yasuji Koyama, Chiba (JP); Toshifumi Matsuda, Chiba (JP); Tadashi Takahashi, Chiba (JP); Kenichiro Matsushima, Chiba (JP); Genryou Umitsuki, Chiba (JP); Tsutomu Masuda, Chiba (JP)

(73) Assignees: Kikkoman Corporation, Noda (JP); Noda Institute for Scientific Research, Noda (JP)

( * ) Notice: Subject to any disclaimer, the term of this patent is extended or adjusted under 35 U.S.C. 154(b) by 359 days.

(21) Appl. No.: 10/325,939

(22) Filed: Dec. 23, 2002

(65) Prior Publication Data

US 2003/0186420 A1 Oct. 2, 2003

(30) Foreign Application Priority Data

Dec. 26, 2001 (JP) .......................................... 2001-395306
Sep. 27, 2002 (JP) .......................................... 2002-283759

(51) Int. Cl.$^7$ ............................ C12N 9/62; C12N 15/57
(52) U.S. Cl. .................. 435/225; 435/320.1; 435/252.3; 536/23.2
(58) Field of Search ............................. 435/225, 320.1, 435/252.3; 536/23.2

(56) References Cited

FOREIGN PATENT DOCUMENTS

WO          99/02705        *   1/1999

OTHER PUBLICATIONS

Endo, F., et al. (1989) J. Biol. Chem. 264(6), 4476–4481.*
Ghosh, M., et al. (1998) J. Bacteriol. 180, 4781–4789.*
Ishii, T., et al. (1996) Biochim. Biochim. Acta 1308, 15–16.*

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

Provided are a protein comprising the amino acid sequence as shown in SEQ ID NO: 2 and having prolidase activities, a prolidase gene coding for the protein, a prolidase gene comprising the nucleotide sequence as shown in SEQ ID NO: 1, recombinant DNA having the gene inserted into vector DNA, and a transformant or transductant comprising the recombinant DNA, and a method for producing prolidase using the transformant or transductant.

The present invention can improve the prolidase through protein engineering. The present invention can be also used for improving microorganisms used in the production of enzymes for food processing and fermented foods.

19 Claims, No Drawings

PROLIDASE AND ITS GENE AND METHOD FOR PRODUCING PROLIDASE

BACKGROUND OF THE INVENTION

1. Field of the Invention

The present invention relates to a protein, prolidase gene, and recombinant DNA and a method for producing prolidase.

2. Background Art

Prolidase (proline dipeptidase, imidodipeptidase, EC3.4.13.9, hereinafter referred to as "prolidase") is an enzyme which hydrolyzes dipeptides having a proline or hydroxyproline residue at its C terminus.

Enzymatic properties of many types of prolidase, from mammalian to *archaebacteria*, have been heretofore determined, and their genes have also been analyzed. For example, known prolidase of mammalian species are those derived from mouse liver [nonpatent literature 1] and human liver [nonpatent literature 2], and known prolidase of bacteria are those derived from *E. coli* [nonpatent literature 3] and *Lactobacillus delbrueckii* [nonpatent literature 4]. Known prolidase of *archaebacteria* include those derived from *Pyrococcus furiosus* [nonpatent literature 5]. Genes of these types of prolidase have also been reported.

Examples of prolidase, which is known for its enzyme only but its genes are not reported, include those derived from *Xanthomonas maltophilia* (patent literature 1).

In Japan, *Aspergillus oryzae* and *Aspergillus sojae*, i.e., *aspergillus* (yellow-green koji mold), have been used in the production of fermented foods such as soybean paste, soy sauce, and rice wine from a long time ago. Based on their long history of use, these microorganisms are particularly important from an industrial point of view because of high enzyme productivity and high safety reliability.

In the *Aspergillus* including yellow-green koji mold, the Genbank (the gene database) contains information concerning only the gene sequence of prolidase derived from *Aspergillus nidulans* (ACCESSION; AJ 296646). However, prolidase activities of purified enzymes and their gene products have not yet been reported.

[Patent literature 1]

JP Patent Publication No. 9-249

[Nonpatent literature 1]

Biochim. Biophys. Acta, 1308 (1), 15–16 (1996)

[Nonpatent literature 2]

J. Biol. Chem., 264 (8), 4476–4481 (1989)

[Nonpatent literature 3]

Nucleic Acids Res., 18 (21), 6439 (1990)

[Nonpatent literature 4]

Mol. Gen. Genet. 247, 494–500 (1995)

[Nonpatent literature 5]

J Bacteriol., 180(18):4781–9, (1998)

When producing soy sauce, a starting material is degraded into a polypeptide by protease, which is generated by *Aspergillus*, the polypeptide is further degraded, by leucine aminopeptidase from the amino terminus and by acidic carboxypeptidase from the carboxyl terminus, into low molecular weight peptides composed mainly of amino acids and dipeptides.

The acidic carboxypeptidase of *Aspergillus* generated is less likely to degrade when the substrate is a tripeptide. It is much less likely to degrade when the substrate is a dipeptide. In particular, peptides having proline at its carboxyl terminus are less likely to be degraded and, thus, these peptides are likely to remain in soy sauce.

In contrast, leucine aminopeptidase is less likely to degrade peptides or acidic peptides having glycine at its amino terminus. Accordingly, these peptides are likely to remain in soy sauce. When proline is present in the peptides, the function of leucine aminopeptidase is suspended because of the presence of Xaa-Pro-peptide bonds in which an amino acid is bound to the proline on its imino group side. In unrefined soy sauce, it is believed that prolyl dipeptidyl peptidase specifically acts on the Xaa-Pro-peptide to release Xaa-Pro, and this allows leucine aminopeptidase to function, thereby releasing and generating amino acids. 13 types of neutral peptides and 13 types of acidic peptides have been reported as dipeptides in soy sauce, the structures thereof have been also deduced, and many Xaa-Pro including Gly-Pro are recognized based on the above-mentioned mechanisms.

Accordingly, degradation of these Xaa-Pro dipeptides can improve the protein degradation rate of soy sauce and an enzymatically-hydrolyzed flavor enhancer. Further, since proline is an amino acid having taste-enhancing properties, taste can be altered, and improvement in flavor can also be expected if Xaa such as Glu-Pro and Asp-Pro are also amino acids with taste enhancing properties.

Ser-Pro, Thr-Pro, Ala-Pro, and Gly-Pro are identified as Xaa-Pro which remains in soy sauce. All of these Xaa are amino acids which enhance sweetness and flavor, and thus improvements in sweetness and flavor of soy sauce can be expected. Accordingly, prolidase derived from microorganisms which relatively easily mass-produce enzymes is desired, and isolation from highly safe microorganisms such as *Aspergillus* is further strongly desired.

SUMMARY OF THE INVENTION

Accordingly, an object of the present invention is to provide a novel prolidase, prolidase gene, and recombinant DNA and a method for producing prolidase, which can degrade Xaa-Pro existing in soy sauce and in enzymatically-hydrolyzed flavor enhancer.

The present inventors have conducted concentrated studies in order to attain the above object. As a result, they succeeded in cloning a novel prolidase gene from yellow-green koji mold, and this has led to the completion of the present invention.

More specifically, the present invention relates to the following.

1. A protein, either:

(a) comprising the amino acid sequence as shown in SEQ ID NO: 2; or (b) comprising an amino acid sequence having one or more amino acids deleted, substituted, or added in the amino acid sequence as shown in SEQ ID NO: 2 and having prolidase activities.

2. A protein comprising an amino acid sequence exhibiting a homology of at least 80% with the full-length amino acid sequence as shown in SEQ ID NO: 2 or a partial fragment thereof and having prolidase activities.

3. A prolidase gene coding for either:

(a) a protein comprising the amino acid sequence as shown in SEQ ID NO: 2; or (b) a protein comprising an amino acid sequence having one or more amino acids deleted, substituted, or added in the amino acid sequence as shown in SEQ ID NO: 2 and having prolidase activities.

4. A prolidase gene coding for a protein, which comprises an amino acid sequence exhibiting a homology of at least 80% with the full-length amino acid sequence as shown in SEQ ID NO: 2 or a partial fragment thereof and has prolidase activities.

5. A prolidase gene comprising either:

(a) DNA comprising the nucleotide sequence as shown in SEQ ID NO: 1; or (b) DNA which hybridizes with DNA comprising a nucleotide sequence complementary to DNA comprising the nucleotide sequence as shown in SEQ ID NO: 1 under a stringent condition and codes for a protein having prolidase activities.

6. Recombinant DNA in which the gene according to 3, 4, or 5 above is inserted into vector DNA.

7. A transformant or transductant comprising the recombinant DNA according to 6 above.

8. A method for producing prolidase comprising culturing the transformant or transductant according to 7 above in a medium and collecting prolidase from the culture product.

DESCRIPTION OF PREFERRED EMBODIMENTS

1. Prolidase of the Invention

The prolidase according to the present invention is a protein comprising the amino acid sequence as shown in SEQ ID NO: 2. This enzyme can be purified from a culture product of yellow-green koji mold, for example, *Aspergillus sojae* or *Aspergillus oryzae*. This enzyme was obtained by expressing a prolidase gene, which was cloned from the yellow-green koji mold and the like in a suitable host vector system.

The prolidase according to the present invention may have one or more amino acids deleted, substituted, or added in the amino acid sequence as shown in SEQ ID NO: 2 as long as it maintains enzymatic activities. Further, the prolidase may be a protein comprising an amino acid sequence which is at least 80%, preferably at least 85%, more preferably at least 90%, and most preferably at least 95% homologous, with the full-length amino acid sequence as shown in SEQ ID NO: 2 or a partial fragment thereof as long as it maintains prolidase activities.

In order to determine the homology between two amino acid sequences or between two nucleotide sequences, sequences are pretreated to optimal conditions for comparison. For example, a gap is inserted into one of the sequences to optimize an alignment with another sequence. Thereafter, an amino acid residue or nucleotide from each site is compared. When the same amino acid residue or nucleotide is present in a specific site in the first sequence with that in the corresponding site in the second sequence, these sequences are identical to each other in that site. Homology between two sequences is indicated by percentage based on the total number of sites (total amino acids or total nucleotides) which are the same between the two sequences.

According to the above principle, the homology between two amino acid sequences or between two nucleotide sequences is determined by the algorithm of Karlin and Altschul (Proc. Natl. Acad. Sci. USA 87: 2264–2268, 1990 and Proc. Natl. Acad. Sci. USA 90: 5873–5877, 1993). The BLAST program using such algorithm was developed by Altschul et al. (J. Mol. Biol. 215: 403–410, 1990). Further, the Gapped BLAST is a program which determines the sequence homology with higher sensitivity than the BLAST (Nucleic Acids Res. 25: 3389–3402, 1997). The above-mentioned program is mainly used for searching the database for a sequence, which is highly homologous with a given sequence. These can be accessed from, for example, a web site of the National Center for Biotechnology Information (U.S.A.) on the Internet.

In the present specification, values, which are determined using the BLAST 2 Sequences software developed by Tatiana A. Tatusova et al. (FEMS Microbiol Lett. 174: 247–250, 1999), are used for indicating the homology between sequences. This software can be accessed from the web site of the National Center for Biotechnology Information (U.S.A.) on the Internet, and is also commercially available. Programs and parameters to be used are as follows. Parameters using the blastp program for the amino acid sequences are Open gap: 11 and extension gap:1 penalties, gap x_dropoff: 50, expect: 10, word size: 3, Filter: ON. Parameters using the blastn program for the nucleotide sequences are Reward for a match: 1, Penalty for a mismatch: −2, Strand option: Both strands, Open gap: 5 and extension gap: 2 penalties, gap $x_{\_dropoff}$: 50, expect: 10, word size: 11, Filter: ON. Both parameters are used as default values in the web site.

When a sequence exhibiting significant homology cannot be found by the BLAST software, a homologous sequence can also be searched for in the database using the more sensitive FASTA software (W. R. Pearson and D. J. Lipman, Proc. Natl. Acad. Sci., 85: 2444–2448, 1988). The FASTA software can be accessed from, for example, the web site of GenomeNet. Default values are also used as parameters in this case. For example, when searching for nucleotide sequences, the nr-nt database is used and the ktup value is set to 6.

In any case, if any value does not exhibit an overlap of at least 30%, at least 50%, or at least 70% of the whole, it cannot be deduced to functionally correlate well with each other, and does not indicate homology between two sequences.

2. Cloning of Prolidase Gene

The prolidase gene according to the present invention can be obtained from, for example, yellow-green koji mold such as *Aspergillus sojae* or *Aspergillus oryzae*, other filamentous fungi, or fungi. More specific examples include *Aspergillus oryzae* RIB40 (*Aspergillus oryzae* var. *viridis* Murakami, anamorph; ATCC42149). These cells are cultured in media having conditions suitable for prolidase generation, and total RNA is collected therefrom in accordance with conventional techniques. Media usable herein include, for example, a bran medium (prepared by adding 2.22 g of deionized water to 2.78 g of wheat bran, and autoclaving at 121° C. for 50 minutes). After culturing in the medium for a suitable period of time, for example, 30 hours, a suitable amount (e.g., 1 g) is transferred to a mortar filled with liquid nitrogen. The transferred cultured cells are then pulverized using a pestle, and total RNA is prepared in accordance with the method by Cathala et al. (DNA, 2(4): 329–335, 1983).

RT-PCR is carried out using the thus obtained total RNA as a template. Any combination of primers may be used as long as it can amplify the prolidase gene according to the present invention. For example, oligonucleotides having sequences as shown in SEQ ID NO: 3 and SEQ ID NO: 4 can be used. RT-PCR can be carried out in accordance with conventional techniques using commercially available kits such as RNA LA-PCR Kit (manufactured by Takara Shuzo Co., Ltd.). DNA comprising the prolidase gene of the invention can be incorporated into a plasmid by, for example, any conventional techniques. The nucleotide sequence of the thus obtained DNA can be determined by the Sanger method using commercially available reagents and DNA sequencers. DNA comprising the prolidase gene according to the present invention and the prolidase gene coded thereby are exemplified as SEQ ID NO: 1 and SEQ ID NO: 2, respectively.

In addition, the prolidase gene according to the present invention may be a gene which codes for a protein comprising an amino acid sequence having one or more amino acids deleted, substituted, or added in the amino acid sequence as shown in SEQ ID NO: 2, as long as it maintains prolidase activities. Such a gene can be obtained through selective hybridization to be described below, as well as through various conventional mutagenesis techniques.

The prolidase gene according to the present invention can be obtained through selective hybridization as described below. Examples of genetic resource include yellow-green koji mold such as *Aspergillus sojae* and *Aspergillus oryzae*. RNA or genomic DNA is prepared from these organisms according to conventional techniques and incorporated into a plasmid or phage, thereby preparing a library. Subsequently, a nucleic acid used as a probe is labeled in accordance with a detection method. Nucleic acids, which are used as probes, may be of sizes, which are long enough to attain sufficient specificity, and examples thereof include a nucleic acid comprising a part or all of at least 100 nucleotides, preferably 200 or more nucleotides, and most preferably 450 or more nucleotides in the sequence as shown in SEQ ID NO: 1. A clone, which hybridizes with the labeled probe under a stringent condition, is then selected from the library. Colony hybridization can be carried out in the case of a plasmid library, and plaque hybridization can be carried out in the case of a phage library. The term "stringent condition" refers to a condition under which specific hybrid signals are differentiated from nonspecific hybrid signals, and the condition is varied depending on the system of hybridization to be used and the type, sequence, and length of probe. Such a condition can be manipulated by changing the hybridization temperature and by changing the temperature and salt level during washing. For example, when a nonspecific hybrid signal is too easily detected, specificity can be enhanced by raising the hybridization and washing temperatures, and if necessary, lowering the salt level during washing. When a specific hybrid signal is not detected, hybrid can be stabilized by lowering the hybridization and washing temperatures, and if necessary, raising the salt level during washing. Researchers versed in the art can easily realize such optimization.

A specific example of a stringent condition is such that hybridization is carried out using a 5×SSC, 1.0% (W/V) blocking reagent for nucleic acid hybridization (manufactured by Boheringer Manheim), 0.1% (W/V) N-lauroyl sarcosine, and 0.02% (W/V) SDS overnight (about 8 to 16 hours), and washing is carried out using 0.5×SSC, 0.1% (W/V) SDS, preferably 0.1×SSC, 0.1 % (W/V) SDS for 15 minutes, twice. The hybridization and washing temperatures are at least 52° C., preferably at least 57° C., more preferably at least 62° C., and most preferably at least 67° C.

A nucleotide sequence, which is at least 80%, preferably at least 85° C., more preferably at least 90%, and most preferably at least 95%, homologous with a portion or all of at least 450 nucleotides in the nucleotide sequence as shown in SEQ ID NO: 1, is considered to code for a protein having substantially equivalent activities with the prolidase according to the present invention.

DNA, which exhibits nucleotide sequence homology as mentioned above or amino acid sequence homology to be coded, can be obtained by employing hybridization as an index as described above. It can also be easily found by searching for a group of DNA with unknown function obtained by genomic nucleotide sequence analysis etc. or public databases using, for example, the BLAST software mentioned above. This search is commonly used by persons skilled in the art.

The thus obtained DNA codes for a protein having prolidase activities. This can be confirmed by incorporating the DNA into a suitable vector, transforming a suitable host, and culturing the transformant, thereby assaying the prolidase activities as described below.

3. Production of Recombinant Vector

The recombinant vector according to the present invention can be obtained by ligating the prolidase gene of the invention to a suitable vector. Any vector can be used as long as it can produce prolidase in the host which is to be transformed. For example, plasmid, cosmid, phage, virus, chromosome-integrated, and artificial chromosome vectors can be used.

The above vector may contain a marker gene, which enables the selection of the transformed cells. Marker genes include, for example, a gene, which complements a host auxotrophy, such as URA3 and niaD or genes resistant to drugs such as ampicillin, kanamycin, or oligomycin. A recombinant vector preferably comprises a promoter, which can express the gene of the present invention in a host cell, or other control sequences (e.g., an enhancer sequence, terminator sequence, or polyadenylation sequence). Specific examples of promoters include, the GAL1 promoter, amyB promoter, and lac promoter. A tag for purification can be applied. For example, a linker sequence is suitably attached downstream of the prolidase gene, and 6 codons or more nucleotide sequences coding for histidine are attached, thereby enabling purification using a nickel column.

4. Obtainment of Transformant

The transformant of the present invention can be obtained by transforming a host with the recombinant vector of the present invention. The host is not particularly limited as long as the prolidase of the present invention can be produced, and examples thereof include, yeasts such as *Saccharomyces cerevisiae* and *Zygosaccharomyces rouxii,* filamentous fungi such as *Aspergillus sojae, Aspergillus oryzae*, and *Aspergillus niger*, and bacteria such as *E. coli* and *Bacillus subtilis*. Transformation can be carried out through a host by conventional techniques. In the case of a yeast, for example, a method using lithium acetate can be employed (Methods Mol. Cell. Biol., 5, 255–269 (1995)). In the case of a filamentous fungus, for example, a method performing protoplastation, followed by the use of polyethylene glycol and calcium chloride can be employed (Mol. Gen. Genet., 218, 99–104 (1989)). When bacteria are used, for example, electroporation can be employed (Methods Enzymol., 194, 182–187 (1990)).

5. Production of Prolidase

The method for producing prolidase of the present invention comprises culturing the transformant or transductant of the present invention and collecting a prolidase protein from the culture product. Media and culture methods can be suitably selected depending on the type of host and the expression control sequence in the recombinant vector. For example, when the host is *Saccharomyces cerevisiae* and the expression control sequence is the GAL1 promoter, a fungus, which has been precultured in a liquid minimal medium containing raffinose as a carbon source, is diluted, inoculated, and cultured in a liquid minimal medium containing galactose and raffinose as a carbon source, thereby producing the prolidase according to the present invention.

When the host is *Aspergillus sojae* and the expression control sequence is the amyB promoter, for example, the prolidase of the present invention can be produced by culturing in a liquid minimal medium containing maltose as a carbon source.

When the host is *E. coli* and the expression control sequence is the lac promoter, for example, the prolidase of the present invention can be produced by culturing in a liquid medium containing IPTG. When the prolidase of the present invention is produced inside or on the surface of a bacterial cell, the bacterial cell is separated from the medium and properly treated. Thus, the prolidase of the present invention can be obtained. For example, when the prolidase is produced on the surface of *Saccharomyces cerevisiae*, the fungus per se is used as an exogenous enzyme to break apart the fungus. Thereafter, low concentration of nonionic surfactants such as Triton X-100, Tween-20, and Nonidet P-40 are introduced, the resulting mixture is centrifuged, and thus the prolidase of the present invention can be collected from the resultant supernatant. When the prolidase of the present invention is produced in the culture solution, a fungus is removed by centrifugation, filtration, and the like, thereby obtaining the prolidase of the present invention. In any case, the prolidase of the present invention can be obtained in higher purity with conventional techniques using ammonium sulfate fractionation, various types of chromatography, alcohol precipitation, ultrafiltration, and the like.

[Method for Assaying Prolidase Activities]

The activity of the prolidase according to the present invention can be assayed by employing Leu-Pro as a substrate and assaying the amino group in the amino acid liberated by the enzymatic action by the acid-ninhydrin method.

Substrate solution: A solution of L-Leu-Pro (manufactured by Sigma) in 20 mM Tris buffer (pH 7.5) to a final concentration of 20 mM Reaction-terminating solution: Glacial acetic acid Ninhydrin reagent: 3% (w/v) ninhydrin (manufactured by Nacalai Tesque Inc.), 60% (v/v) glacial acetic acid, 40% (v/v) phosphoric acid 390 $\mu$l of 20 mM Tris buffer (pH 7.5) is added to 10 $\mu$l of enzyme solution, and the mixture is preincubated at 37° C. for 5 minutes. Thereafter, 100 $\mu$l of substrate solution is added thereto, the reaction is allowed to proceed at 37° C. for 15 minutes, and 500 $\mu$l of reaction-terminating solution is added to terminate the enzyme reaction. Further, 500 $\mu$l of ninhydrin reagent is added, and the mixture is boiled at 100° C. for 10 minutes and then cooled. The absorbance at 515 nm is then measured. The amount of enzyme generating 1$\mu$ mole of proline per minute under the above condition is determined as 1 unit (U).

The present invention will be described in more detail with reference to the following examples, although the present invention is not limited to these examples.

EXAMPLES

1: Cloning of Prolidase Gene of *Aspergillus oryzae*

About 100,000 conidiospores of *Aspergillus oryzae* RIB40 (*Aspergillus oryzae* var. *viridis* Murakami, anamorph; ATCC42149) were inoculated in 5 g of bran medium (described above) in a 150 ml conical flask. The inoculated conidiospores were then subjected to stationary culture at 30° C. for 30 hours to obtain a culture product. The culture product was put into a liquid nitrogen-cooled mortar, and liquid nitrogen was then added into the culture product. Thereafter, the culture product was thoroughly pulverized using a pestle, which was also cooled by liquid nitrogen. Total RNA was extracted from the pulverized fungus in accordance with the method by Cathala et al. [DNA, 2(4): 329–335, 1983]. Further, the DNA-free kit (manufactured by Amibion) was used to perform DNase I treatment to degrade the DNA present therein. 1.0 ug of obtained total RNA was used as a template to perform RT-PCR using the Marathon cDNA Amplification Kit (manufactured by Clontech).

A primer attached to the kit having an adaptor sequence on the 3'-side of oligo (dT) was used as a primer for reverse transcription, and reverse transcription was performed at 42° C. for 60 minutes.

Subsequently, a cocktail containing RNaseH, DNA polymerase, DNA ligase, and the like is added to the reverse transcript in accordance with the instructions attached to the kit, and the mixture was allowed to react at 16° C. for 90 minutes. Thereafter, T4DNA polymerase was further added, and the mixture was allowed to react at 16° C. for 50 minutes. Thus, a library of double-stranded cDNA was synthesized.

Adaptor DNA, DNA ligase, and the like were then added to the reaction product, and a library of double-stranded cDNA, to which the adaptor was ligated, was synthesized. The composition of each reaction solution and the reaction conditions were thoroughly in accordance with the attached instructions.

Subsequently, PCR was performed using the primers as shown in SEQ ID NO: 3 and SEQ ID NO: 4 and the library of double-stranded cDNA obtained above as a template. Amplification was carried out immediately before the initiation codon on the 5'-side and immediately after the termination codon on the 3' side. A restriction site was added to the 5'-side of each primer for easy cloning (e.g., KpnI was introduced into the primer as shown in SEQ ID NO: 3 and XhoI was introduced into the primer as shown in SEQ ID NO: 4). Takara EX Taq DNA Polymerase (manufactured by Takara Shuzo Co., Ltd.) was used as a heat-resistant DNA polymerase, and the reaction solution was composed in accordance with the instructions attached to the polymerase.

PCR was carried out at 94° C. for 2 minutes, followed by 30 cycles of: 94° C. for 30 seconds; 55° C. for 30 seconds; and 72° C. for 2 minutes, then continued at 72° C. for 5 minutes. A the amplification product was subjected to 0.7% agarose gel electrophoresis, and as a result, about 1.4 kb band was observed. GeneAmp 5700 Sequence detection system (manufactured by PE Applied Biosystems) was used as a thermal cycler, and the temperature was controlled based on calculation control.

TOPO TA Cloning Kit (manufactured by Invitrogen) was then used to incorporate the amplification product into pCR2.1TOPO vector, and *E. coli* TOP10F' (manufactured by Invitrogen) was transformed to obtain a transformant. The plasmid was extracted from the transformant using the QIAprep Spin Miniprep Kit (manufactured by QIAGEN). The Thermo Sequenase Cycle Sequencing Kit (manufactured by Amersham Pharmacia Biotech) was used to perform sequence reaction, and the nucleotide sequence was determined using the LI-COR MODEL 4200L Sequencer (manufactured by LI-COR).

As a result, the DNA sequence of about 1.4 kb open reading frame (ORF) as shown in SEQ ID NO: 1 was observed. This plasmid, pPEPP2036, was deposited at the International Patent Organism Depositary of the National Institute of Advanced Industrial Science and Technology under the accession number FERM BP-7825. The nucleotide sequence from the initiation codon to the immediately before the termination codon of the clone contained in pPEPP2036 is shown in SEQ ID NO: 1. The above nucleotide sequence was analyzed and, as a result, this DNA was found to code for a protein comprising 467 amino acid residues. This amino acid sequence is shown in SEQ ID NO: 2.

Further, this amino acid sequence was subjected to searches for highly homologous sequences therewith in a public database on amino acid sequences. NCBI blastp (http://www.ncbi.nlm.nih.gov/BLAST/) was used for the searches, and the nr database was designated. As a result, there was no matching sequence, and the prolidase of *Aspergillus nidulans* exhibited the highest homology (GenBank: AJ296646), i.e., a homology of 75%.

Sequences, which are highly homologous with the nucleotide sequence as shown in SEQ ID NO: 1, was searched for. NCBI blastn (http://www.ncbi.nlm.nih.gov/BLAST/) was used for the search, and the nr database was designated. As a result, there was no matching sequence, and a gene coding for the prolidase of *Aspergillus nidulans*, above-mentioned, exhibited the highest homology (GenBank: AJ296646). The sequence homology of the whole coded region was inspected by the analytical software GENETYX-WIN Ver. 5.0, and 1,401 nucleotides showed a sequence homology of 69%.

2. Expression of Prolidase cDNA

Using the plasmid pPEPP2036 as a template and using the primers as shown in SEQ ID NO: 5 which contained initiation codons and using the primers as shown in SEQ ID NO: 6 which contained a termination codons, full-length prolidase cDNA was amplified by PCR.

Subsequently, this PCR product was TA-cloned into a yeast expression vector pYES2.1-V5-his-TOPO (manufactured by Invitorogen) to prepare plasmid pYES2036. This plasmid can induce the expression of a protein of interest (prolidase) by galactose. INVSc1 (Genotype: MATa, his3Δ1, leu2, trp1-289, ura3-52/MATα, his3Δ1, leu2, trp1-289, ura3-52) was used as a host, and a yeast host was transformed using the above plasmid pYES2036 by the lithium acetate method. Selective media used were Yeast Nitrogenbase free of 0.67% amino acid (manufactured by Difco), 2% raffinose (manufactured by Wako Pure Chemicals Industries, Ltd.), and Yeast Synthetic Dropout Medium Supplement free of uracil (manufactured by SIGMA). The lithium acetate method was carried out in accordance with the description in "Tanpakushitsu Jikken Purotokoru (Experimental Protocol on Protein)—Kinou Kaiseki Hen (Functional Analysis)"(p.63–88, Saibou Kougaku (Cell Technology), Separate Volume, Shujunsha Co. Ltd.).

Subsequently, the obtained transformant was used to express a protein in accordance with the protocol attached to the pYES2.1-V5-his-TOPO vector. A 200 ml conical flask equipped with a baffle was used to inoculate the transformant from the colony into 20 ml of selective medium, and the inoculated transformant was subjected to gyratory culture at 30° C. at 140 rpm for approximately 14 hours. This was designated as a starter culture. Subsequently, the turbidity of the starter culture ($OD_{600}$) was measured, and the starter culture was inoculated in the protein expression inductive medium to bring the initial turbidity ($OD_{600}$) to 0.4. Culture in the protein expression inductive medium was carried out by shake culture using a 500 ml Sakaguchi flask in 50 ml of medium at 30° C. at 140 rpm. The protein expression inductive medium which was used, contained 1% raffinose and 2% galactose (manufactured by Wako Pure Chemicals Industries, Ltd.) as a carbon source for selective medium.

48 hours after the initiation of induction, the culture solution was centrifuged at 3,000 rpm for 10 minutes, and the supernatant was determined to be a fraction of extracellular secretory protein and the precipitate was determined to be a fraction of bacterial cell. To prepare a bacterial cell suspension, isovolumes of extraction buffer (20 mM tris-HCl, pH 7.5, 45 mM KCl, 25 mM glycerol) were added to each pellet and suspended in the fraction of bacterial cell. Equivolumes of glass beads were added to the suspension and vigorously stirred for 15 minutes. Thereafter, centrifugation was carried out at 15,000 rpm for 20 minutes. The supernatant was determined to be a fraction of an intracellular secretory protein, and the precipitate was determined as a residue fraction on the bacterial cell surface.

The obtained fraction of the intracellular secretory protein was determined to be a crude enzyme solution, and the prolidase activities were assayed. The results are shown in Table 1. Numerical values in the table indicate the prolidase activities (mU/ml) per ml of culture solution that is 48 hours after the induction of protein expression. The "vector" indicates a transformant of plasmid pYES2.1-V5-his-TOPO, and "2036" indicates a transformant of plasmid pYES2036. "(−)" indicates that culture was carried out in a protein nonexpression inductive galactose free medium and "(+)" indicates that culture was carried out in a protein expression inductive medium containing galactose.

The transformant of the plasmid pYES2036, cultured in the protein expression inductive medium, exhibited prolidase activities of approximately 22 times higher than that of the transformant of the plasmid pYES2.1-V5-his-TOPO. Even if compared to the case where the transformant of the plasmid pYES2036 was cultured in the protein non-expression inductive galactose free medium, approximately 31 times higher prolidase activity was observed.

Accordingly, the gene obtained by the present invention was the prolidase gene, and the use of the present gene enables the mass-production of prolidase.

TABLE 1

| Vector(+) | 2036(−) | 2036(+) |
|---|---|---|
| 3.8 | 2.7 | 84.1 |

Industrial Applicability

The present invention provides a protein, prolidase gene, recombinant DNA and a method for producing prolidase.

The present invention can improve the activities through protein engineering. The present invention can be also used for improving microorganisms used in the production of enzymes for food processing and fermented foods.

What is claimed is:

1. An isolated polynucleotide that encodes a polypeptide that hydrolyzes dipeptides having a proline or hydroxyproline residue at their C-terminus:
   (a) which encodes a polypeptide having at least 95% homology to SEQ ID NO: 2, or
   (b) which hybridizes to the complement of SEQ ID NO: 1 under highly stringent conditions, wherein stringent conditions comprise hybridization using 5×SSC and 0.02% SDS at 52° C. and washing in 0.1×SSC and 0.1% SDS at 67° C.

2. The polynucleotide of claim 1, which has at least 95% homology to SEQ ID NO: 1.

3. The polynucleotide of claim 1, which hybridizes to the complement of SEQ ID NO: 1 under highly stringent conditions.

4. The polynucleotide of claim 1, which is SEQ ID NO: 1 or a fragment of SEQ ID NO: 1 that encodes a polypeptide that hydrolyzes dipeptides having a proline or hydroxyproline residue at their C-terminus.

5. A vector comprising the polynucleotide of claim 1.

6. The vector of claim 5, further comprising a marker gene, promoter and/or control sequence.

7. A host cell transformed with the vector of claim 5.

8. The host cell of claim 7 which is a yeast.

9. The host cell of claim 7 which is a filamentous fungi.

10. The host cell of claim 7 which is a bacterium.

11. A method for producing an isolated polypeptide that hydrolyzes dipeptides having a proline or hydroxyproline residue at their C-terminus comprising:
    culturing the host cell of claim 7 for a time and under conditions suitable for production of said polypeptide, and
    recovering or collecting said polypeptide.

12. An isolated polypeptide that hydrolyzes dipeptides having a proline or hydroxyproline residue at their C-terminus encoded by a polynucleotide:
    (a) which encodes a polypeptide having at least 95% homology to SEQ ID NO: 2, or
    (b) which hybridizes to the complement of SEQ ID NO: 1 under stringent conditions,
    wherein stringent conditions comprise hybridization using 5×SSC and 0.02% SDS at 52° C. and washing in 0.1×SSC and 0.1% SDS at 67° C.

13. The polypeptide of claim 12, which is encoded by a polynucleotide that has at least 95% homology to SEQ ID NO: 1.

14. The polypeptide of claim 12 that is encoded by a polynucleotide which hybridizes to the complement of SEQ ID NO: 1 under highly stringent conditions.

15. The polypeptide of claim 12, which comprises SEQ ID NO: 2 or a fragment of SEQ ID NO: 2 that hydrolyzes dipeptides having a proline or hydroxyproline residue at their C-terminus.

16. A composition comprising the polypeptide of claim 12.

17. The composition of claim 16 which is a food or a starting material for a food.

18. The composition of claim 17, which is soy sauce or an enzymatically-hydrolyzed flavor enhancer.

19. A method for producing a food comprising:
    contacting a food starting material with the polypeptide of claim 12 or with a host cell expressing said polypeptide for a time and under conditions suitable for enzymatic hydrolysis of dipeptides having a proline or hydroxyproline residue at their C-terminus in the food starting material,
    recovering the hydrolyzed food starting material, and optionally,
    further processing and/or purifying said hydrolyzed food starting material.

* * * * *

SEQUENCE LISTING

<160> NUMBER OF SEQ ID NOS: 6

<210> SEQ ID NO 1
<211> LENGTH: 1401
<212> TYPE: DNA
<213> ORGANISM: Aspergillus oryzae RIB40
<220> FEATURE:
<221> NAME/KEY: CDS
<222> LOCATION: (1)..(1401)

<223> OTHER INFORMATION:

<400> SEQUENCE: 1

```
atg gct act gtg gat gat ata ctg aca ggc aaa tat cct gcc aaa tcc        48
Met Ala Thr Val Asp Asp Ile Leu Thr Gly Lys Tyr Pro Ala Lys Ser
1               5                   10                  15 cat gcg cgc cgg gtt gcc cag ctt ctt cag gcc cat cac gga caa ggt        96
His Ala Arg Arg Val Ala Gln Leu Leu Gln Ala His His Gly Gln Gly
            20                  25                  30 gct cct ggg gtt att tac ttg gaa gcc cag aaa act cgt ctt ata gag       144
Ala Pro Gly Val Ile Tyr Leu Glu Ala Gln Lys Thr Arg Leu Ile Glu
        35                  40                  45 gat aat gac gaa ccg atg cca ttc agg caa cga cgt ttc ttt tac tac       192
Asp Asn Asp Glu Pro Met Pro Phe Arg Gln Arg Arg Phe Phe Tyr Tyr
    50                  55                  60 ttg tca ggg tgc tcg cta cca gat tcg tac ttg atc tac gac att aac       240
Leu Ser Gly Cys Ser Leu Pro Asp Ser Tyr Leu Ile Tyr Asp Ile Asn
65                  70                  75                  80 gct gac aag ctc act ctg ttt ata cct cct att gat gcg gaa gag gta       288
Ala Asp Lys Leu Thr Leu Phe Ile Pro Pro Ile Asp Ala Glu Glu Val
                85                  90                  95 atc tgg tca ggg ctt ccc ctc tcc gcg gat gag gct atg aag ctt tac       336
Ile Trp Ser Gly Leu Pro Leu Ser Ala Asp Glu Ala Met Lys Leu Tyr
            100                 105                 110 gat gtt gac tgt gta ctt gcg gcg act gaa gtc aat gcc act ctt cgt       384
Asp Val Asp Cys Val Leu Ala Ala Thr Glu Val Asn Ala Thr Leu Arg
        115                 120                 125 tct att ggc tca gca tat ggt ggc aat gcc gta gct ttt gcg atc gct       432
Ser Ile Gly Ser Ala Tyr Gly Gly Asn Ala Val Ala Phe Ala Ile Ala
130                 135                 140 gat cag gtc tct agc gga gcg gaa ttc caa ggt ttt gca gaa acc aag       480
Asp Gln Val Ser Ser Gly Ala Glu Phe Gln Gly Phe Ala Glu Thr Lys
145                 150                 155                 160 ctt tcc gtc ctg aag gaa gct att gaa aag gcg cgc gtc gtg aaa gac       528
Leu Ser Val Leu Lys Glu Ala Ile Glu Lys Ala Arg Val Val Lys Asp
                165                 170                 175 gaa tat gag atc gct ctt ttg cga aag gct aat gat atc tct gcc aag       576
Glu Tyr Glu Ile Ala Leu Leu Arg Lys Ala Asn Asp Ile Ser Ala Lys
            180                 185                 190 gca cat att gct gct ata aga gct tca aag act gca gta aac gag cgt       624
Ala His Ile Ala Ala Ile Arg Ala Ser Lys Thr Ala Val Asn Glu Arg
        195                 200                 205 gag att gag ggc gcg ttt atc gcg acg tgt atc gct cat ggt gct cgt       672
Glu Ile Glu Gly Ala Phe Ile Ala Thr Cys Ile Ala His Gly Ala Arg
    210                 215                 220 gag caa tct tat cac ccc atc gtt gct tgt ggt gca aac ggt gcc acc       720
Glu Gln Ser Tyr His Pro Ile Val Ala Cys Gly Ala Asn Gly Ala Thr
225                 230                 235                 240 ctt cac tat ggc aag aat gat gat gac ctg acg gat cct gca acg aag       768
Leu His Tyr Gly Lys Asn Asp Asp Asp Leu Thr Asp Pro Ala Thr Lys
                245                 250                 255 caa agg aag aat aac att ctc att gac gct gga ggc gaa tac cgg gca       816
Gln Arg Lys Asn Asn Ile Leu Ile Asp Ala Gly Gly Glu Tyr Arg Ala
            260                 265                 270 tat tgc tcg gat ata acg cgc gtg ttc cct tta ggt ggg agc ttc aca       864
Tyr Cys Ser Asp Ile Thr Arg Val Phe Pro Leu Gly Gly Ser Phe Thr
        275                 280                 285 aaa gaa acc cgc cag att tat gag atc gtc cta caa atg cag ctg gaa       912
Lys Glu Thr Arg Gln Ile Tyr Glu Ile Val Leu Gln Met Gln Leu Glu
    290                 295                 300
```

```
tgc atc gca atg ctc aaa gga gat gtg caa tgg gag gat gtg cat gcg      960
Cys Ile Ala Met Leu Lys Gly Asp Val Gln Trp Glu Asp Val His Ala
305                 310                 315                 320 cat gca cac cgt gtt gcc atc aag ggc ttg ctc gct ttg ggg att cta     1008
His Ala His Arg Val Ala Ile Lys Gly Leu Leu Ala Leu Gly Ile Leu
                325                 330                 335 agt ggc tcc gag gat gaa ttg ttc gag aag aga atc agc gta gcg ttt     1056
Ser Gly Ser Glu Asp Glu Leu Phe Glu Lys Arg Ile Ser Val Ala Phe
            340                 345                 350 ttc cct cat ggt ctc ggg cac tat ctt ggg atg gat acg cat gac act     1104
Phe Pro His Gly Leu Gly His Tyr Leu Gly Met Asp Thr His Asp Thr
        355                 360                 365 ggg ggc aat cca aac tat ggc gac aag gat acc atg ttt aaa tac ctc     1152
Gly Gly Asn Pro Asn Tyr Gly Asp Lys Asp Thr Met Phe Lys Tyr Leu
370                 375                 380 cgt gtc aga ggc cgt ctg cct gta ggt tcc gtt atc act gtt gaa cca     1200
Arg Val Arg Gly Arg Leu Pro Val Gly Ser Val Ile Thr Val Glu Pro
385                 390                 395                 400 ggg atc tac ttc tgc cgc ttc att atc gat ccc tat act caa tct cca     1248
Gly Ile Tyr Phe Cys Arg Phe Ile Ile Asp Pro Tyr Thr Gln Ser Pro
                405                 410                 415 gag ctg ggg aag tac att aat acc act gtc ctg gag cgg tat tgg atg     1296
Glu Leu Gly Lys Tyr Ile Asn Thr Thr Val Leu Glu Arg Tyr Trp Met
            420                 425                 430 gtg ggg ggc gtt cgt atc gaa gat aat att cac atc acc aaa gat ggc     1344
Val Gly Gly Val Arg Ile Glu Asp Asn Ile His Ile Thr Lys Asp Gly
        435                 440                 445 cac gaa aat ttg acc aca gcg ccg aaa gcc ata gaa gaa atg gaa agc     1392
His Glu Asn Leu Thr Thr Ala Pro Lys Ala Ile Glu Glu Met Glu Ser
450                 455                 460 ttg gcc ttg                                                          1401
Leu Ala Leu
465
```

<210> SEQ ID NO 2
<211> LENGTH: 467
<212> TYPE: PRT
<213> ORGANISM: Aspergillus oryzae RIB40

<400> SEQUENCE: 2

```
Met Ala Thr Val Asp Asp Ile Leu Thr Gly Lys Tyr Pro Ala Lys Ser
1               5                   10                  15

His Ala Arg Arg Val Ala Gln Leu Leu Gln Ala His Gly Gln Gly
            20                  25                  30

Ala Pro Gly Val Ile Tyr Leu Glu Ala Gln Lys Thr Arg Leu Ile Glu
        35                  40                  45

Asp Asn Asp Glu Pro Met Pro Phe Arg Gln Arg Arg Phe Phe Tyr Tyr
    50                  55                  60

Leu Ser Gly Cys Ser Leu Pro Asp Ser Tyr Leu Ile Tyr Asp Ile Asn
65                  70                  75                  80

Ala Asp Lys Leu Thr Leu Phe Ile Pro Pro Ile Asp Ala Glu Glu Val
                85                  90                  95

Ile Trp Ser Gly Leu Pro Leu Ser Ala Asp Glu Ala Met Lys Leu Tyr
            100                 105                 110

Asp Val Asp Cys Val Leu Ala Ala Thr Glu Val Asn Ala Thr Leu Arg
        115                 120                 125

Ser Ile Gly Ser Ala Tyr Gly Gly Asn Ala Val Ala Phe Ala Ile Ala
    130                 135                 140
```

```
Asp Gln Val Ser Ser Gly Ala Glu Phe Gln Gly Phe Ala Glu Thr Lys
145                 150                 155                 160

Leu Ser Val Leu Lys Glu Ala Ile Glu Lys Ala Arg Val Val Lys Asp
            165                 170                 175

Glu Tyr Glu Ile Ala Leu Leu Arg Lys Ala Asn Asp Ile Ser Ala Lys
        180                 185                 190

Ala His Ile Ala Ala Ile Arg Ala Ser Lys Thr Ala Val Asn Glu Arg
    195                 200                 205

Glu Ile Glu Gly Ala Phe Ile Ala Thr Cys Ile Ala His Gly Ala Arg
210                 215                 220

Glu Gln Ser Tyr His Pro Ile Val Ala Cys Gly Ala Asn Gly Ala Thr
225                 230                 235                 240

Leu His Tyr Gly Lys Asn Asp Asp Leu Thr Asp Pro Ala Thr Lys
            245                 250                 255

Gln Arg Lys Asn Asn Ile Leu Ile Asp Ala Gly Gly Glu Tyr Arg Ala
            260                 265                 270

Tyr Cys Ser Asp Ile Thr Arg Val Phe Pro Leu Gly Ser Phe Thr
275                 280                 285

Lys Glu Thr Arg Gln Ile Tyr Glu Ile Val Leu Gln Met Gln Leu Glu
    290                 295                 300

Cys Ile Ala Met Leu Lys Gly Asp Val Gln Trp Glu Asp Val His Ala
305                 310                 315                 320

His Ala His Arg Val Ala Ile Lys Gly Leu Leu Ala Leu Gly Ile Leu
                325                 330                 335

Ser Gly Ser Glu Asp Glu Leu Phe Glu Lys Arg Ile Ser Val Ala Phe
            340                 345                 350

Phe Pro His Gly Leu Gly His Tyr Leu Gly Met Asp Thr His Asp Thr
        355                 360                 365

Gly Gly Asn Pro Asn Tyr Gly Asp Lys Asp Thr Met Phe Lys Tyr Leu
    370                 375                 380

Arg Val Arg Gly Arg Leu Pro Val Gly Ser Val Ile Thr Val Glu Pro
385                 390                 395                 400

Gly Ile Tyr Phe Cys Arg Phe Ile Ile Asp Pro Tyr Thr Gln Ser Pro
                405                 410                 415

Glu Leu Gly Lys Tyr Ile Asn Thr Thr Val Leu Glu Arg Tyr Trp Met
            420                 425                 430

Val Gly Gly Val Arg Ile Glu Asp Asn Ile His Ile Thr Lys Asp Gly
        435                 440                 445

His Glu Asn Leu Thr Thr Ala Pro Lys Ala Ile Glu Glu Met Glu Ser
    450                 455                 460

Leu Ala Leu
465

<210> SEQ ID NO 3
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
tgtggtacca tggctactgt ggatgatata ctg                              33

<210> SEQ ID NO 4
<211> LENGTH: 33
```

```
<212> TYPE: DNA
<213> ORGANISM: Artificial Sequence
<220> FEATURE:
<223> OTHER INFORMATION: SYNTHETIC DNA

<400> SEQUENCE: 4
cgactcgagc tacaaggcca agctttccat ttc                          33

<210> SEQ ID NO 5
<211> LENGTH: 27
<212> TYPE: DNA
<213> ORGANISM: Artificial Sequence
<220> FEATURE:
<223> OTHER INFORMATION: SYNTHETIC DNA

<400> SEQUENCE: 5
accatggcta ctgtggatga tatactg                                 27

<210> SEQ ID NO 6
<211> LENGTH: 27
<212> TYPE: DNA
<213> ORGANISM: Artificial Sequence
<220> FEATURE:
<223> OTHER INFORMATION: SYNTHETIC DNA

<400> SEQUENCE: 6
caaggccaag ctttccattt cttctat                                 27
```